(12) United States Patent
Robertson et al.

(10) Patent No.: US 6,547,771 B2
(45) Date of Patent: Apr. 15, 2003

(54) NON-INVASIVE FEMALE URINARY DEVICE

(75) Inventors: Janet Robertson, Hayden, ID (US); Charles W. Robertson, Hayden, ID (US)

(73) Assignee: Caring Hands, Inc., Hayden, ID (US)

(*) Notice: Subject to any disclaimer, the term of this patent is extended or adjusted under 35 U.S.C. 154(b) by 40 days.

(21) Appl. No.: 09/846,050

(22) Filed: Apr. 30, 2001

(65) Prior Publication Data

US 2001/0049520 A1 Dec. 6, 2001

Related U.S. Application Data

(60) Provisional application No. 60/200,909, filed on May 1, 2000.

(51) Int. Cl.$^7$ .............................................. A61M 1/00
(52) U.S. Cl. ...................... 604/317; 604/329; 604/347; 4/144.1; 4/144.2; 4/144.3; 4/144.4
(58) Field of Search ................................ 604/317, 329, 604/346–347, 327; 4/144.1–144.4; 141/333

(56) References Cited

U.S. PATENT DOCUMENTS

| | | | | |
|---|---|---|---|---|
| 2,100,888 A | * | 11/1937 | Vine | 226/38 |
| 2,490,969 A | | 12/1949 | Kinyon | 4/110 |
| 3,512,185 A | | 5/1970 | Ellis | 4/110 |
| 3,613,122 A | | 10/1971 | Gross et al. | 4/110 |
| 3,964,111 A | | 6/1976 | Packer | 4/110 |
| 4,023,216 A | | 5/1977 | Li | 4/110 |
| 4,496,355 A | | 1/1985 | Hall et al. | 604/327 |
| 4,528,703 A | | 7/1985 | Kraus | 4/144.2 |
| 4,626,249 A | | 12/1986 | Hamey | 604/329 |
| 4,751,751 A | * | 6/1988 | Reno | 141/337 |
| 4,756,029 A | | 7/1988 | Zieve et al. | 4/144.4 |
| 4,784,654 A | | 11/1988 | Beecher | 604/329 |
| 4,815,151 A | | 3/1989 | Ball | 4/144.3 |
| 4,846,819 A | | 7/1989 | Welch | 604/329 |
| 4,937,890 A | | 7/1990 | Tafur | 4/144.4 |
| 4,986,823 A | | 1/1991 | Anderson et al. | 604/329 |
| 5,091,998 A | * | 3/1992 | Irazabal | 141/333 |
| 5,632,736 A | | 5/1997 | Block | 604/329 |
| 5,687,429 A | | 11/1997 | Rahlff | 4/144.4 |
| 5,893,176 A | | 4/1999 | Magiera et al. | 4/144.4 |
| 5,966,748 A | * | 10/1999 | Young et al. | 4/144.4 |

FOREIGN PATENT DOCUMENTS

| EP | WO 82/02831 | 9/1982 |
|---|---|---|
| GB | 2 240 717 A | 8/1991 |

* cited by examiner

*Primary Examiner*—Gregory Huson
*Assistant Examiner*—Amanda Flynn
(74) *Attorney, Agent, or Firm*—Robert L. Shaver; Frank J. Dykas; Stephen M. Nipper

(57) ABSTRACT

A non-invasive female urinary device allows a woman to urinate in a standing or sitting position. The non-invasive female urinary device provides a scoop portion designed to be positioned adjacent to the woman's body, and is sized to fit between the labia majora. The scoop gathers urine as it is produced, with little or no loss due to spillage. A generally tubular body is attached at an upstream first end to the scoop portion. The device is made of six flat sides to allow the woman to control the orientation of the device. The logo on one of the sides provides a tactile reference, allowing the woman to orient the device without the need for visual input. A flow concentrator is attached to a downstream second end of the tubular body, and has a generally rectangular opening that narrows the stream of urine to result in a smooth and continuous stream.

16 Claims, 1 Drawing Sheet

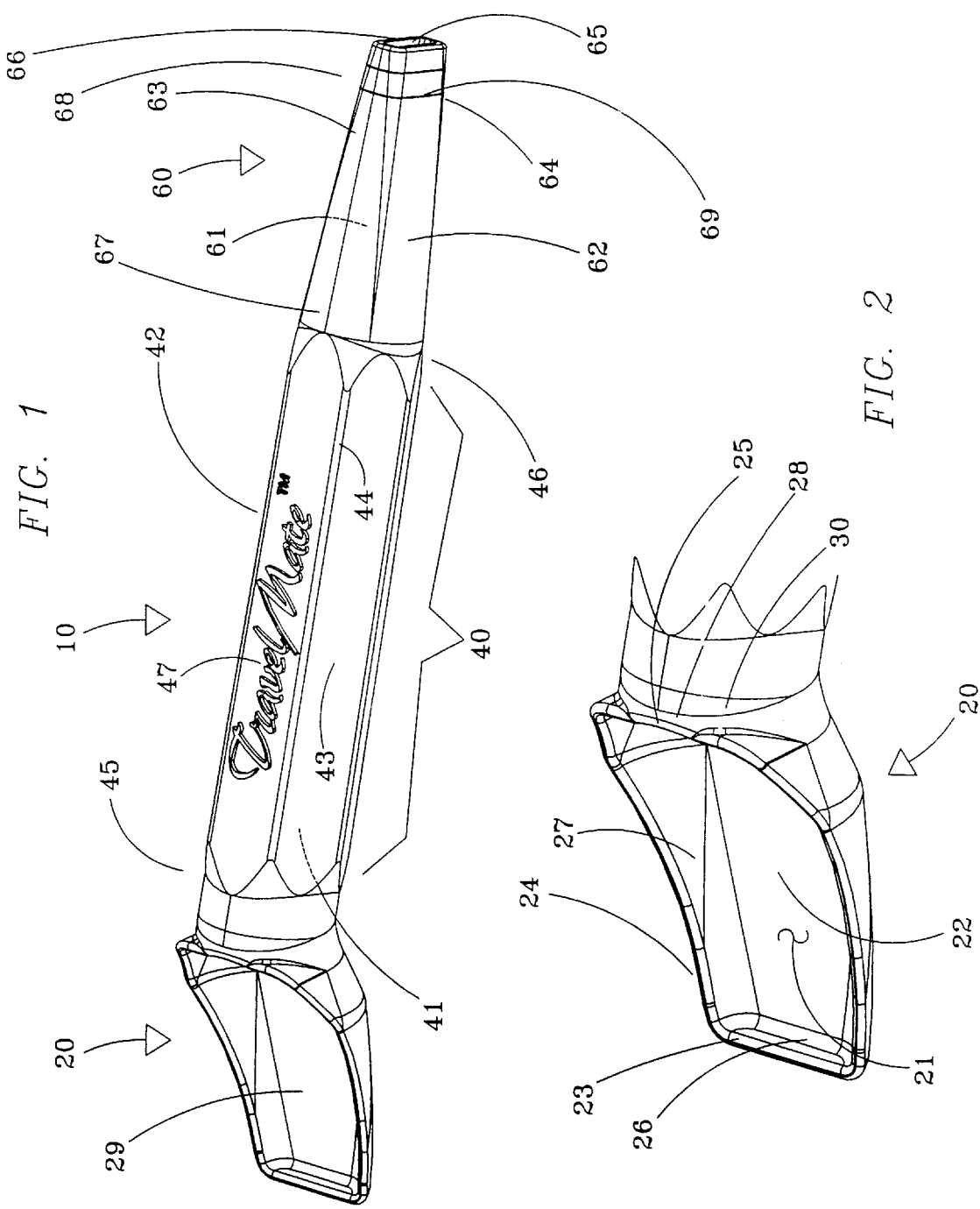

NON-INVASIVE FEMALE URINARY DEVICE

REFERENCE TO RELATED APPLICATION

This application is a utility application claiming the priority of provisional application Ser. No. 60/200,909, filed May 1, 2000, entitled Non-Invasive Female Urinary Device.

DESCRIPTION

BACKGROUND OF THE INVENTION

Field of the Invention. The present invention generally relates to urinary devices, and more particularly relates to non-invasive female urinary devices.

Background Information. An increasing number of women are spending a greater amount of time outdoors. This is due to a number of reasons, including involvement in such sports as hunting and fishing, and also due to time spent in jobs such as construction and the armed forces. As a result of the time spent outdoors, women have increasingly realized that toilet facilities can be absent when needed. While men have the ability to urinate behind the cover of a few trees in almost total privacy, women must disrobe to a far greater extent, and therefore enjoy far less privacy. This problem is sometimes exacerbated, particularly in the sporting, construction and military environment, by the likelihood that far more men will be present than women.

Additionally, there are many situations where women must be able to urinate in a seated position, where toilet facilities are not present. For example, a number of women suffer from disabilities or diseases that result in use of a wheelchair and that result in the need to urinate frequently. Where a wheelchair or similar mobility-disabling condition is present, it may be difficult or impossible to access an available toilet. Where frequent urination is an issue, this condition may be exacerbated by travel, particularly in small aircraft without toilet facilities. As a result, these conditions and many other similar conditions make the ability to urinate in a hygienic manner while in a seated position extremely advantageous.

As a result, there is a need for a female urinary device that is non-invasive and enables a woman to urinate standing or sitting in places where a conventional toilet is inconvenient due to physical disability or unavailable.

SUMMARY OF THE INVENTION

The present invention is directed to an apparatus that satisfies the above needs. A novel non-invasive female urinary device is disclosed that allows a woman to urinate in a standing or sitting position, with only minimal disrobing and which results in little or no transfer of urine to the clothes or body of the woman.

The non-invasive female urinary device of the present invention provides some or all of the following structures.

(A) A scoop portion is designed to be positioned adjacent to the woman's body, and is sized to fit between the labia majora. The scoop gathers urine as it is produced, with little or no loss due to spillage.

(B) A generally tubular body, defining an interior passage, is attached at a first end to the scoop portion. A preferred body is made of six flat sides to allow the woman to control the orientation of the device, thereby preventing the rotation of the scoop and the spillage of urine. In a preferred embodiment of the invention, the top side of the six sides defines a logo molded or printed on the surface of the top side. The logo provides a tactile reference, allowing the woman to orient the device without the need for visual input.

(C) A flow concentrator is attached to a second end of the tubular body. The flow concentrator narrows the stream of urine to result in a smooth and continuous stream, without the separation of small droplets which may be moved by air currents in undesirable directions. The discharge opening is defined by a generally rectangular rim which results in a preferred flow pattern consistent with the highest level of hygiene possible.

It is therefore a primary advantage of the present invention to provide a novel non-invasive female urinary device that allows a woman to urinate while standing up or while sitting in places where a conventional toilet is inconvenient or unavailable, with an absolute minimum of disrobing.

Another advantage of the present invention is to provide a novel non-invasive female urinary device that is comfortable to use, and that results in leak-free contact by a scoop portion that fits between the labia majora.

A still further advantage of the present invention is to provide a novel non-invasive female urinary device that provides a flow concentrator having an opening defined by a generally rectangular rim that results in a smooth and continuous urine stream consistent with the highest level of personal hygiene, without the separation of small droplets which may be moved by air currents in undesirable directions.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE DRAWINGS

FIG. 1 is a perspective view of a version of the non-invasive female urinary device of the invention.

FIG. 2 is an enlarged perspective view of the scoop portion of the non-invasive female urinary device.

DESCRIPTION OF THE PREFERRED EMBODIMENTS

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Referring in general to FIG. 1, a non-invasive female urinary device constructed in accordance with the principles of the invention is seen. A preferred version of the non-invasive female urinary device 10 includes a scoop 20 which is sized to fit between the labia majora, thereby making a leak-free connection. The scoop defines a bowl-like cavity 21 which, in operation, receives urine. The scoop is attached to a first end of a body 40 defining a lengthwise-oriented interior passage. A second end of the body is attached to a flow concentrator 60 having an opening defined by a generally rectangular rim which results in a smooth and continuous urine stream consistent with the highest level of personal hygiene, without the separation of small droplets which may be moved by air currents in undesirable directions.

A preferred version of the non-invasive female urinary device 10 is constructed of plastic, typically through an injection molding process. As a result, the device is lightweight, low-cost and easily cleaned. While certain parts of the device may be referred to individually, such as the scoop 20, the body 40 and the flow concentrator 60, it is important to note that in a preferred construction, the entire device would be made in one piece for reasons of economy and quality.

As seen, in FIG. 1, a scoop portion 20, is designed to be positioned adjacent to the woman's body, and is sized to fit between the labia majora. The scoop gathers urine as it is produced, with little or no loss due to spillage.

Continuing to refer to FIG. 1, the scoop defines a bowl-like cavity 21. A low front wall 26, variable height left and right sidewalls 27, a back wall 28 and the base 29 form the generally four-sided bowl shaped cavity 21.

The upper rim of the bowl-like cavity, comprising a lower rim 23, left and right side rims 24 and an upper rim 25, defines a generally rectangular inlet or opening 22. The inlet is oriented substantially as seen in FIG. 1 during use, in manner which results in a fluid-tight fit between the labia majora.

Behind the back wall 28 is a transition collar 30 which joins the scoop to a first end of the body 40 of the non-invasive female urinary device 10.

As seen in FIG. 1, a generally tubular body 40, defining an interior passage 41, is attached at an upstream first end 45 to the scoop 20. In a preferred embodiment, the scoop and body are attached at an angle of 15 degrees, but this could be altered, as desired. The preferred body is made of a sidewall 42 comprising six flat sides 43 separated by rounded corners 44. The flat sides allow the woman to control the orientation of the device 10, thereby preventing the rotation of the scoop 20 and the spillage of urine. In a preferred embodiment of the invention, the top side of the six sides defines a logo 47 molded or printed on the surface of the top side. The logo provides a tactile reference, allowing the woman to orient the device without the need for visual input.

The length of the body should be sufficient to extend past the woman's outer clothing, and is typically three or more inches in length.

A flow concentrator 60 is attached to a downstream second end 46 of the tubular body 40. The flow concentrator narrows the stream of urine to result in a smooth and continuous stream, without the separation of small droplets which may be moved by air currents in undesirable directions.

An interior passage 61 is defined within left and right angled sidewalls 62, a tapered top 63 and a tapered bottom 64. Due to the tapered design of the flow concentrator, the crosssectional area of the upstream end 67 is greater than the cross-section of the downstream end 68.

As seen in FIG. 1, an opening 65 in the end of the downstream end of the flow concentrator is defined by a generally rectangular rim 66. In use, the shape of the opening tends to result in a smooth and continuous stream consistent with the highest levels of personal hygiene possible. This flow pattern prevents splattering and creation of smaller droplets that are particularly susceptible to unwanted movement in windy conditions.

Continuing to refer to FIG. 1, two scribe marks 69 are indented onto the end of the flow concentrator. Where desired, the tip of the flow concentrator may be cut off at either scribe mark, thereby increasing the cross-sectional area of the opening and resulting in a corresponding increase in the rate of flow possible. Cutting along either scribe mark will result in a newly defined opening having a generally rectangular rim consistent with the smooth and coherent stream.

In use, the non-invasive female urinary device 10 allows a woman to urinate in a standing or sitting position, with limited need to disrobe. Sufficient clothing is loosened to allow the scoop 20 to be positioned between the labia majora. The lower rim 23 is positioned just below the opening to the urethra. The opening 65 is positioned lower in elevation than the scoop 20 to result in flow in the correct direction.

During urination, urine is transferred from the bowl-like cavity 21 of the scoop into the interior passage 41 of the tube-like body 40. The urine is somewhat turbulent as it moves through the passage 41. However, the diameter of the interior passage is sufficient to accommodate the stream of urine moving toward the flow concentrator. As the urine moves into the interior passage 61 of the flow concentrator 60, the flow becomes sufficiently regular in direction that when the stream passes through the opening 65 in the downstream end of the flow concentrator, the stream is collected and coherent.

After urination, the lower rim 23 may be moved across the area of skin adjacent to the opening of the urethra, thereby removing any residual urine.

After use, the urinary device is easily cleaned by flushing with water and disinfectant.

In some applications, the non-invasive female urinary device 10 may be used with standard latex tubing and a urinary drainage bag. In such an application, the latex tubing would be attached to the flow concentrator, thereby enabling the collection of the urine for disposal.

The previously described versions of the present invention have many advantages, including a primary advantage providing a novel non-invasive female urinary device that allows a woman to urinate while standing up or while sitting in places where a conventional toilet is inconvenient or unavailable, with an absolute minimum of disrobing.

Another advantage of the present invention is to provide a novel non-invasive female urinary device that is comfortable to use, and that results in leak-free contact by a scoop portion that fits between the labia majora.

A still further advantage of the present invention is to provide a novel non-invasive female urinary device that provides a flow concentrator having an opening defined by a generally rectangular rim that results in a smooth and continuous urine stream consistent with the highest level of personal hygiene, without the separation of small droplets which may be moved by air currents in undesirable directions.

Although the present invention has been described in considerable detail and with reference to certain preferred versions, other versions are possible. For example, while certain portions of the urinary device have been described to have specific shapes, it is clear that some variation could be introduced, while still keeping within the teachings of the invention. Therefore, the spirit and scope of the appended claims should not be limited to the description of the preferred versions disclosed.

In compliance with the U.S. Patent Laws, the invention has been described in language more or less specific as to methodical features. The invention is not, however, limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

We claim:

1. A non-invasive female urinary device for aiding sanitary urination by a female user from a standing, seated, or lying position, comprising:
   a scoop portion with a first end and a second end, which is configured to fit between the labia majora of said female user's body, and shaped to form a watertight seal thereon, with an inlet for collecting urine which exits said female user, an outlet for said urine to pass from said scoop portion, and with said scoop portion comprising a left and right sidewall, a rear wall connecting said left and rear sidewalls on said first end, and a generally straight rim connecting said left and right sidewalls on said second end;
   a device body with a first end and a second end, with said first end connected to said scoop portion second end, for conducting said urine from said outlet of said scoop portion to said second end of said device body; and
   a flow concentrator with a first end and a second end, in which said first end of said flow concentrator is attached to said second end of said device body, and said second end of said flow concentrator forms a flow concentrator outlet, in which said flow concentrator tapers in diameter from said first end to said second end, for conducting said urine from said urinary device in a forcefully directed stream.

2. The non-invasive female urinary device of claim 1 in which said device body is comprised of a plurality of flat sides with edges, which are joined to each other at said edges, which together provide a positive grip for orientation control of the device.

3. The non-invasive female urinary device of claim 2 which is comprised of six flat sides with edges, which are joined to each other at said edges, and which together provide a positive grip for orientation control of the device.

4. The non-invasive female urinary device of claim 1 in which said scoop portion is attached to said device body at an angle of 10 to 20 degrees.

5. The non-invasive female urinary device of claim 4 in which said scoop portion is attached to said device body at an angle of approximately 15 degrees.

6. The non-invasive female urinary device of claim 2 in which one of said flat sides is configured to be positioned superior to said other sides when in use, and in which said superior side includes a tactile reference for aid in positioning said female urinary device.

7. The non-invasive female urinary device of claim 1 in which said straight rim of said scoop portion further includes a cleaning edge for removing traces of liquid from said female user.

8. The non-invasive female urinary device of claim 1 in which said inlet to said scoop is generally trapezoidal in shape, formed by said straight rim, said left and said right sidewalls, and by a generally straight rear wall.

9. The non-invasive female urinary device of claim 1 in which said left and right sidewalls of said scoop further comprise a curved top edge forming two sides of said scoop inlet.

10. The non-invasive female urinary device of claim 9 in which said curved top edge of said left and right sidewalls of said scoop follow a curve based approximately on a 5 inch radius.

11. The non-invasive female urinary device of claim 1 in which said outlet from said flow concentrator is a generally rectangular rim.

12. The non-invasive female urinary device of claim 1 in which said second end of said flow concentrator is configured to have a generally rectangular cross section.

13. The non-invasive female urinary device of claim 12 which is configured so that a portion of said second end of said flow concentrator may be removed to form a new flow concentrator outlet which allows for increased urine flow, while retaining a generally rectangular cross section.

14. The non-invasive female urinary device of claim 13 which further includes one or more scribe lines which encircle said second end of said flow concentrator and which are adjacent said outlet on said flow concentrator, and which serve as breakaway joints or guides marks for shortening said flow concentrator and making said flow concentrator outlet larger in diameter.

15. The non-invasive female urinary device of claim 1 in which said device body is of a uniform diameter from said first end to said second end of said device body.

16. A non-invasive female urinary device for aiding sanitary urination by a female user from a standing, seated, or lying position, comprising:
   a scoop portion with a first end and a second end, which is configured to fit between the labia majora of said female user's body, and shaped to form a watertight seal thereon, with an inlet for collecting urine in which said inlet to said scoop is generally trapezoidal in shape, formed by said straight rim, said left and said right sidewalls, and by a generally straight rear wall, an outlet for said urine to pass from said scoop portion, and with said scoop portion comprising a left and right sidewall, a rear wall connecting said left and rear sidewalls on said first end, and a generally straight rim connecting said left and right sidewalls on said second end;
   a device body with a first end and a second end, with said first end connected to said scoop portion second end, in which said device body is comprised of a plurality of flat sides with edges, which are joined to each other at said edges, which together provide a positive grip for orientation control of the device, in which said scoop portion is attached to said device body at an angle of 10 to 20 degrees, for conducting said urine from said outlet of said scoop portion to said second end of said device body; and
   a flow concentrator with a first end and a second end, in which said first end of said flow concentrator is attached to said second end of said device body, and said second end of said flow concentrator forms a generally rectangular flow concentrator outlet, in which said flow concentrator tapers in diameter from said first end to said second end, for conducting said urine from said urinary device in a forcefully directed stream.

* * * * *